(12) United States Patent
Hagenmeyer

(10) Patent No.: US 6,478,824 B1
(45) Date of Patent: Nov. 12, 2002

(54) JOINT-ENDOPROSTHESIS AND FIXATION METHOD FOR THE SEAT THEREOF

(76) Inventor: Klaus Hagenmeyer, Egerstrasse 4, D-869 1 Dieber (DE)

( * ) Notice: Subject to any disclaimer, the term of this patent is extended or adjusted under 35 U.S.C. 154(b) by 0 days.

(21) Appl. No.: 09/744,056

(22) PCT Filed: Jun. 29, 1999

(86) PCT No.: PCT/EP99/04489

§ 371 (c)(1),
(2), (4) Date: Mar. 13, 2001

(87) PCT Pub. No.: WO00/03663

PCT Pub. Date: Jan. 27, 2000

(30) Foreign Application Priority Data

Jul. 17, 1998 (DE) .......................................... 198 32 272

(51) Int. Cl.[7] .................................................. A61F 2/36
(52) U.S. Cl. .................................. 623/23.16; 623/23.15
(58) Field of Search ............................ 601/1, 2, 46, 47; 623/22.11, 23.15, 23.25, 23.26

(56) References Cited

U.S. PATENT DOCUMENTS

| 5,496,256 | A | | 3/1996 | Bock et al. ..................... 601/2 |
| 5,524,624 | A | | 6/1996 | Tepper et al. ................... 601/2 |
| 5,556,372 | A | | 9/1996 | Talish et al. .................... 601/2 |
| 5,730,705 | A | * | 3/1998 | Talish et al. .................... 601/2 |
| 5,752,924 | A | | 5/1998 | Kaufman et al. ............... 601/2 |
| 6,022,349 | A | * | 2/2000 | McLeod et al. ............... 606/58 |
| 6,200,255 | B1 | * | 3/2001 | Yu ................................. 600/1 |
| 6,231,528 | B1 | * | 5/2001 | Kaufman et al. ........... 600/439 |

* cited by examiner

Primary Examiner—Corrine McDermott
Assistant Examiner—Hieu Phan
(74) Attorney, Agent, or Firm—Cesari & McKenna, LLP

(57) ABSTRACT

The invention relates to a joint endoprosthesis and a method for fixing the seat thereof. The endoprosthesis has a shaft that is anchored in the marrow cavity of a tubular bone, and an ultra source that is placed in or on the shaft and the radiation characteristics of which enable ultrasound waves to reach a gap between the spongiosa of the tubular bone and the surface of the external covering of the shaft. The associated method applies impinging ultrasound waves upon the gap.

11 Claims, 4 Drawing Sheets

JOINT-ENDOPROSTHESIS AND FIXATION METHOD FOR THE SEAT THEREOF

BACKGROUND OF THE INVENTION

The invention relates to a joint-endoprosthesis having a shaft that is anchored in the marrow cavity of a tubular bone. The invention further relates to a method of fixing the seat of a joint-endoprosthesis shaft in the marrow cavity of a tubular bone.

Such joint-endoprostheses are known and serve, for instance, to replace shoulder, arm, hip, knee or foot joints of a human being. All those artificial joints have in common that they comprise at least one conical shaft, which is driven into the marrow cavity of the corresponding tubular bone for fixing the same when the endoprosthesis is inserted. In most cases the surface of the external covering of the shaft comprises supporting ribs bringing about a ratchet-like adherence of the shaft in the marrow cavity of the tubular bone when the shaft is driven in. By additionally feeding small soft bits of spongiosa into the indentations of the supporting ribs the primary stabilization and the ability of the bone to grow in after the insertion is supported.

It has, however, shown that the feeding of the spongiosa bits not always results in the desired stabilization of the endoprosthesis shaft. On one hand, this may be due to a non-optimal fit of the shaft in view of the rarely ideally formed bone and, on the other hand, to the metabolism process being different from patient to patient and the different osteogenesis connected therewith. Because of this, or also as a result of inadvertent movements when wearing the already inserted joint-endoprothesis, luxations of the endoprosthesis with a dislocation by several centimeters may occur. In such cases another operation is often required, which in most cases takes place in two steps.

An ultrasound device comprising a transportable operating element and an ultrasound head is known from U.S. Pat. No. 5,730,705, which can be placed upon the skin of the patient in the proximity of the region to be impinged with ultrasound. The propagation of the ultrasound waves and the formation of shear waves along the shaft of the endoprosthesis are illustrated in FIGS. 4 and 5 thereof. Thus, said known ultrasound device serves to impinge the gap between the spongiosa of the tubular bone and the surface of the external covering of the endoprosthesis shaft with ultrasound.

SUMMARY OF THE INVENTION

Reliable fixation of the joint endoprosthesis shaft in the bone is thus a primary concern. It is that problem which this invention addresses, its objective being an improved joint endoprosthesis of the type described above whereby a more stable fixation of the shaft in the bone is attainable.

Given a joint-endoprosthesis of the above-described kind said object is solved in accordance with the invention by providing an ultrasound source on or in the shaft, the radiation characteristics of which enable the ultrasound waves to reach a gap between the spongiosa of the tubular bone and the surface of the external covering of the shaft.

The object underlying the invention is moreover provided in accordance with the invention by a method of the afore-mentioned kind, wherein the gap between the spongiosa of the tubular bone and the surface of the external covering of the endoprosthesis shaft is impinged with ultrasound generated by an ultrasound source disposed on or in the shaft.

In view of the healing of bone fractures the invention makes use of the gained knowledge that the osteocytes required for the healing of a fracture multiply by the introduction of ultrasound waves into the fracture gap thereby resulting in a faster, better and more stable healing of the fracture gap. The background of said effect is that the ultrasound stimulates the cell walls of the mesenchyma cells to oscillate, which results in a desired proliferation. In respect of the use of ultrasound it is essential that it is introduced into the fracture gap, where it impinges and stimulates the spongiosa and the bone marrow, whereas it would be otherwise more or less reflected by the corticalis of the bone.

The connection of the joint-endoprosthesis shaft with an ultrasound source according to the invention and the special radiation characteristics thereof directed at the gap between the spongiosa and the shaft results in the desired stimulation of the cell walls during the operation of the ultrasound source and in the proliferation of the osteocytes. The ultrasound source may thereby be disposed externally on the shaft, or—which most likely is the preferred embodiment—may be part of the shaft or may at least be integrated in the same. A plurality of ultrasound sources may also be distributed over the circumference of the joint-endoprosthesis shaft, if a regular impingement of the gap between the shaft and the bone can only thereby be obtained.

Advantageous embodiments of the inventions are described in the subclaims.

Thus it is, for instance, provided that the ultrasound source is arranged such that the shaft serves as an oscillation carrier in the form of a resonance body. It is the goal of said improved embodiment to achieve a regular impingement of the gap between the shaft and the bone with ultrasound by the shaft uniformly introducing ultrasound into the gap.

Each ultrasound source is preferably part of an ultrasound module with an inherent voltage source so that, for operating the ultrasound source, no voltage has to be supplied from outside, in other words, a corresponding terminal on the patient's body or even an operation are not necessary.

In order to avoid a large heat generation through the impingement of the gap with high-frequency ultrasound (approximately 1.5 MH) it is provided that the ultrasound module comprises a multi-vibrator by means of which the ultrasound source is pulsed, i.e. operated intermittently. A ratio of 2:8 between working time to non-working time has proved to be practicable.

It is the goal of the following improved embodiment to keep the ultrasound module ready to work for an as long as possible period of time without the requirement of a new operation and to make it externally operable by means of a remote control. For this purpose it is provided that the ultrasound module comprises a switch for switching the ultrasound source on/off, and a sensor for the remote-controlled activation of the switch by means of a signal transmitter. Said signal transmitter may work in the known fashion likewise on an ultrasound basis or on an infrared basis.

In order to make sure what the ultrasound module can be inserted in the shaft of the joint-endoprosthesis as easily as possible prior to the insertion of the joint-endoprosthesis, for example, for activating the voltage source beforehand, the ultrasound module is provided with a housing being accessible from outside by means of a cover plate in the shaft. Said cover plate can be removed by detaching some screws.

Despite a minimization of the current consumption of the ultrasound module it may be necessary to design the voltage source such that it can be charged from outside.

The improved embodiments of the method according to the invention provide a pulsing of the ultrasound such that an impingement lasting about 200 μsec is followed by a break of about 800 μsec.

BRIEF DESCRIPTION OF DRAWINGS

Two preferred embodiments of the invention in the form of a hip joint-endoprosthesis will hereinafter be explained in more detail by means of a drawing, wherein.

DETAILED DESCRIPTION OF THE INVENTION

Figure 1:
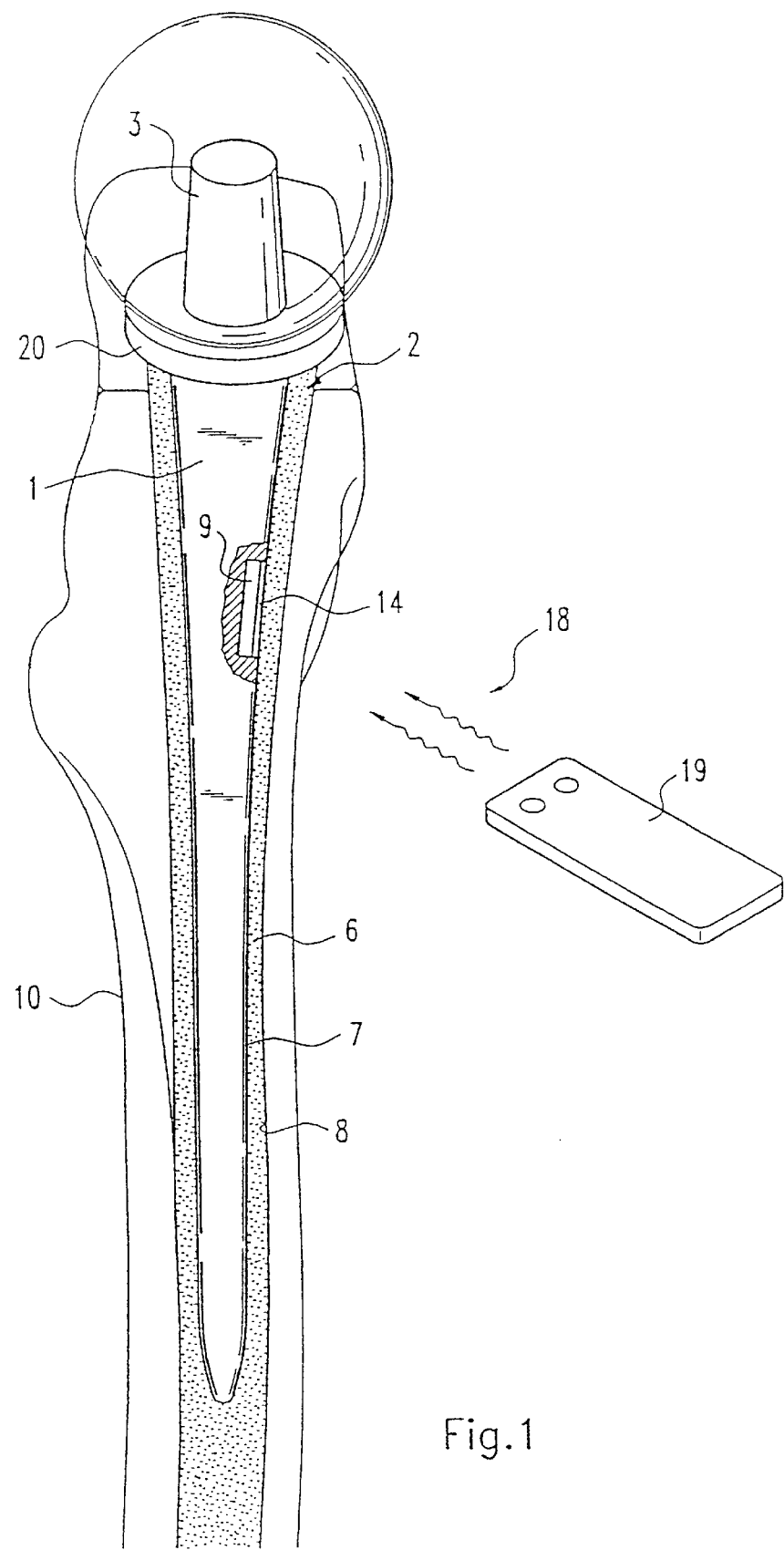
FIG. 1 shows a schematic ventral-dorsal vertical profile through a resected femora section with an inserted hip joint-endoprosthesis.

FIG. 1 shows a schematic ventral-dorsal vertical profile through a resected femora section 4, in the marrow cavity 2 of which a shaft 1 of a hip joint-endoprosthesis is inserted. The shaft 1 is joined upwardly in the usual manner by a truncated socket 3 covering the resected femora stump with a collar 20. A gap 6 is illustrated—in an exaggerated size for better understanding—between the surface of the external covering 7 of the shaft 1 and the inner circumference of the marrow cavity 2. Such a gap may occur due to a non-optimal fit when, for example, the hip joint-endoprosthesis is inserted, or due to a luxation with the result of a dislocation caused by an inadvertent movement or excessive sportive exercise by the person wearing the endoprosthesis. It is known that the tubular bone 4 of the femora section has a relatively soft porous inner layer, the spongiosa 8. Moreover, the marrow cavity 2 and thus the gap 6 is filled with bone marrow.

Figure 5:
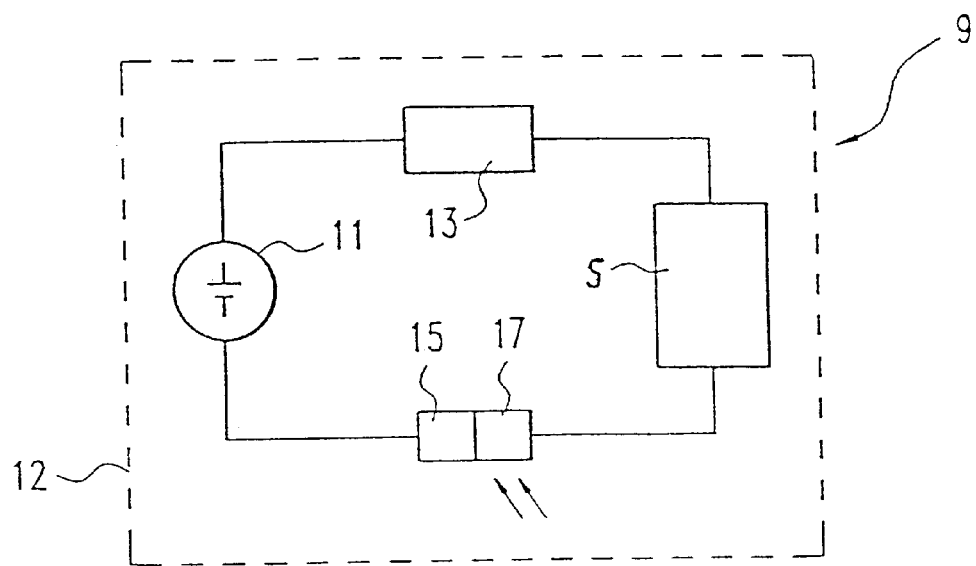
FIG. 5 shows a schematic diagram of an ultra sound module.

An ultrasound module 9 is disposed in the endoprosthesis shaft 1 comprising an ultrasound source 5, a voltage source 11, a multi-vibrator 13, a switch 15 and a sensor 17 in a housing 12 as essential elements compare FIG. 5). The housing 12 is sealed with an ultrasound-permeable cover plate 14 on the surface of the external covering 7 of the shaft 1. During the operation of the ultrasound module the radiation characteristics of the ultrasound source 5 enable ultrasound waves to reach the gap 6 between the spongiosa 8 of the tubular bone 4 and the surface of the external covering 7 of the shaft 1 so as stimulate the spongiosa 8 and the (non-illustrated) bone marrow to proliferate osteocytes.

The switching on and off of the ultrasound source 5 is preferably effected by means of a remote control in the form of a signal transmitter 19, which emits infrared or ultrasound radiation 18 via the sensor 17 for activating the switch 15.

Figure 2:
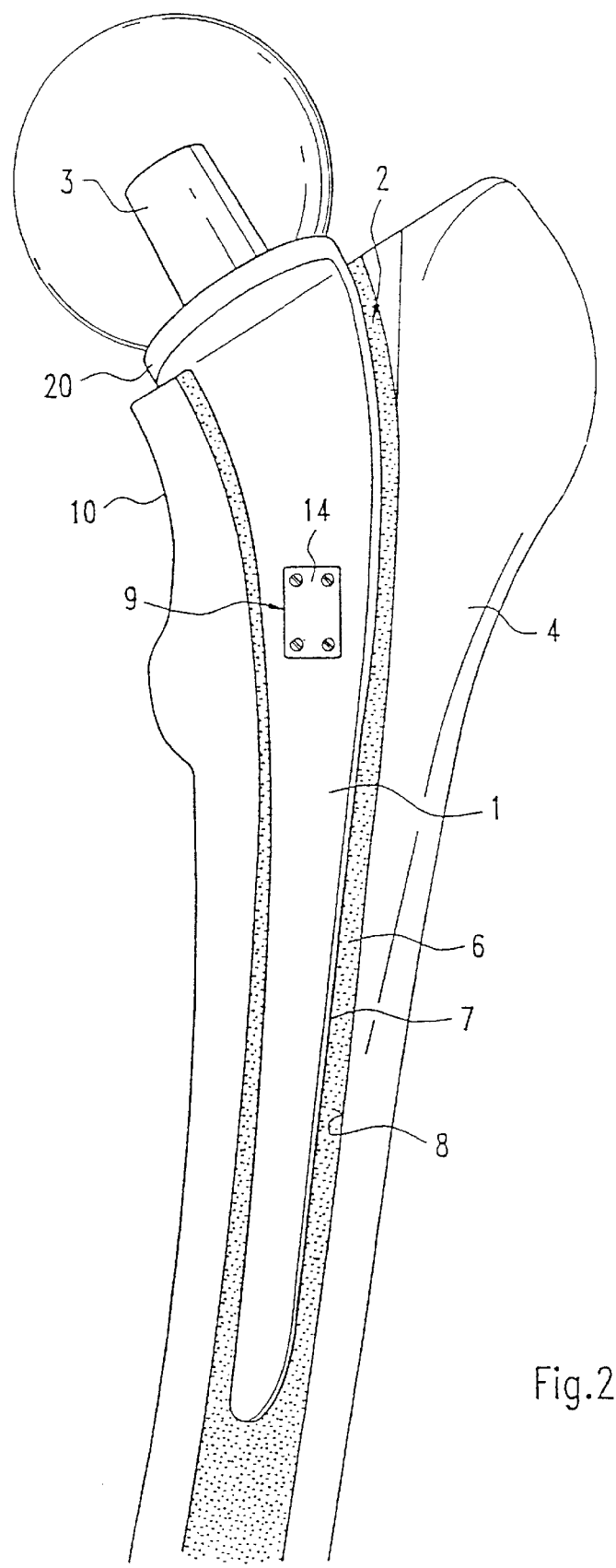
FIG. 2 shows a schematic lateral-medical vertical profile according to FIG. 1.
Figure 3:
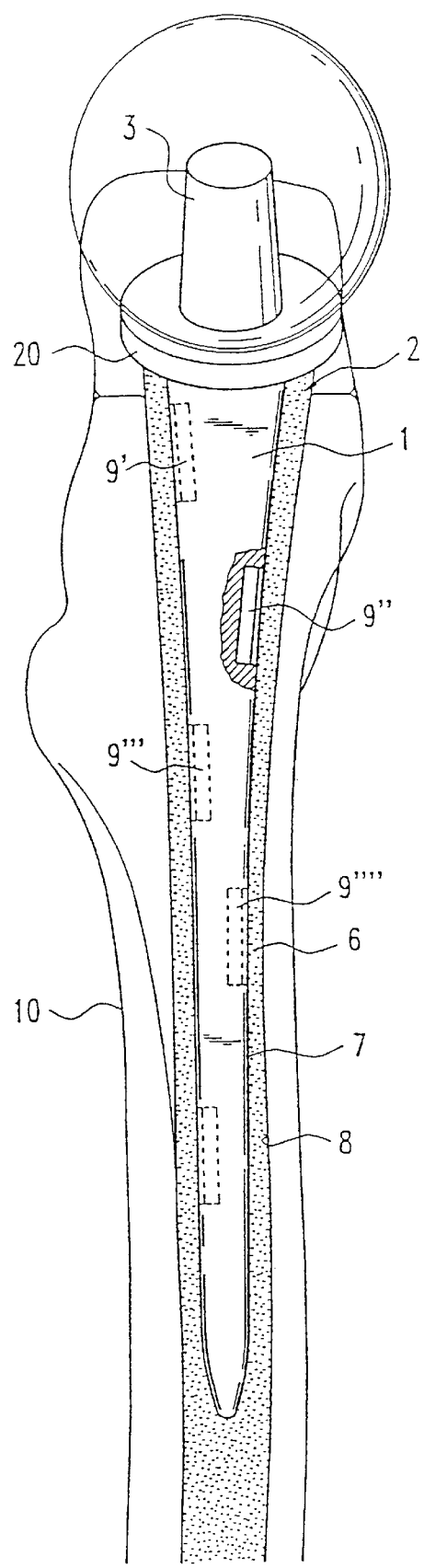
FIG. 3 shows an illustration according to FIG. 1, however, comprising several ultrasound sources or, respectively, ultrasound modules distributed over the circumference of the shaft.

FIG. 2 shows a schematic lateral-media vertical profile through the tubular bone 4 according to FIG. 1 enabling the view onto the cover plate 14 of the ultrasound module 9.

With the goal to supply the gap 6 around the shaft 1 with ultrasound energy as uniformly as possible, a shaft of the joint-endoprosthesis is, according to a second embodiment, provided, having a plurality of ultrasound sources 5', 5", 5'" . . . distributed over the circumference of shaft 1. Each ultrasound source again forms part of an ultrasound module 9', 9", 9'" . . . , all of which may be switched on or off in the above-explained manner.

Figure 4:
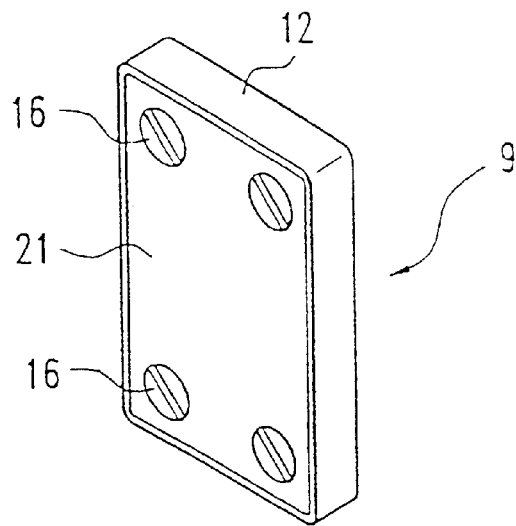
FIG. 4 shows a schematic perspective view of an ultrasound module according to the detail "X" of FIG. 2.

FIG. 4 shows a perspective illustration of an ultrasound module 9 having a housing 12 and a front plate 21 attached on the housing 12 by means of screws 16. Said front plate 21 may be identical to the cover plate 14 in the mounted state of the ultrasound module 9.

FIG. 5 shows a schematic diagram of an ultrasound module 9. As was already described above, the module comprises a voltage source 11, a multi-vibrator 13, an ultrasound source 5, a switch 15 as well as a sensor 17, all of which are accommodated in the housing 12. In view of the cover plate 14 or, respectively, in view of the endoprosthesis shaft 1 the ultrasound source 5 is thereby arranged such that an optimum exposure to sonic waves of the gap 6 with the spongiosa 8 contained therein and the bone marrow is secured.

The method according to the invention is once more briefly explained by means of FIG. 1: By using the knowledge that the formation of osteocytes, which are, for instance, necessary for the healing of a bone fracture, is supported by the impingement of the mesenchyma cells with ultrasound, the method according to the invention provides, for making the seat of a joint-endoprosthesis shaft 1 in the marrow cavity 2 of a tubular bone 4 more stable, that the gap 6 between the spongiosa 8 of the tubular bone 4 and the surface of the external covering 7 of the shaft 1 is impinged with ultrasound by means of an ultrasound source 5. For avoiding an excessive generation of heat in the gap 6 the impingement with ultrasound is pulsed so that after an impingement lasting about 200 μsec a break of about 800 μsec occurs. A usual output of the ultrasound source 5 is about 30 mW with a sound frequency of about 1.5 MHz.

What is claimed is:

1. A joint-endoprosthesis comprising
    a shaft (1) having an external covering (7) and being anchored in the marrow cavity (2) of a tubular bone (4) having spongiosa (8)
    an ultrasound source (5) on or in the shaft (1), said ultrasound source having radiation characteristics which enable ultrasound waves to reach a gap (6) between the spongiosa (8) of the tubular bone (4) and the external covering (7) of the shaft (1).

2. The joint-endoprosthesis according to claim 1, wherein the ultrasound (5) is arranged such that the shaft (1) serves as an oscillation carrier.

3. The joint-endoprosthesis according to claim 1, wherein a plurality of ultrasound sources (5', 5", 5'" . . . ) are distributed around the shaft (1) or disposed in or on the shaft (1).

4. The joint-endoprosthesis according to one of the claims 1 to 3, wherein
    each ultrasound source (5', 5", 5'" . . . ) is part of an ultrasound module (9) having an inherent voltage source (11).

5. The joint-endoprosthesis according to claim 4, wherein the ultrasound module (9) comprises a multi-vibrator (13) with which the ultrasound source (5) is pulsed.

6. The joint-endoprosthesis according to claim 4, wherein the ultrasound module (9) comprises a switch (15) for switching on/off the ultrasound source (5) and a sensor (17) for the remote-controlled activation of the switch (15) by means of a signal transmitter.

7. The joint-endoprosthesis according to claim 4, wherein the ultrasound module (9) comprises a housing (12) accessible from outside through a cover plate (14) in the shaft (1).

8. The joint-endoprosthesis according to claim 4, wherein the voltage source (11) is charged from outside.

9. A method of strengthening the retention of a joint endoprosthesis as in claim 1, including the step of impinging said ultrasound waves upon said gap (6).

10. The method according to claim 9, wherein the impingement with ultrasound is pulsed.

11. The method according to claim 10, wherein an impingement lasting about 200 $\mu$sec is followed by a break of about 800 $\mu$sec.

* * * * *